(12) United States Patent
Fritz et al.

(10) Patent No.: US 7,449,326 B2
(45) Date of Patent: Nov. 11, 2008

(54) SYSTEM FOR SIMPLE NUCLEIC ACID ANALYSIS

(75) Inventors: Michael Fritz, Biblis (DE); Volker Gerstle, Lorsch (DE); Herbert Harttig, Altrip (DE); Juergen Schwab, Ketsch (DE); Joachim Steinbiss, Lorsch (DE); Andreas Rauscher, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 55 days.

(21) Appl. No.: 09/780,206

(22) Filed: Feb. 9, 2001

(65) Prior Publication Data

US 2002/0018998 A1 Feb. 14, 2002

(30) Foreign Application Priority Data

Feb. 11, 2000 (DE) .................... 100 06 214

(51) Int. Cl.
- *C12M 3/00* (2006.01)
- *C12Q 1/68* (2006.01)
- *C12P 19/34* (2006.01)
- *C07H 21/02* (2006.01)

(52) U.S. Cl. .................. 435/283.1; 435/6; 435/91.2; 536/23.1

(58) Field of Classification Search ............. 536/22.1, 536/23.1; 435/286.5, 288.5, 6, 291, 283.1, 435/91.2

See application file for complete search history.

(56) References Cited

U.S. PATENT DOCUMENTS

| | | | | |
|---|---|---|---|---|
| 5,415,839 A | * | 5/1995 | Zaun et al. ............... | 422/64 |
| 5,593,838 A | * | 1/1997 | Zanzucchi et al. ......... | 435/6 |
| 5,635,358 A | | 6/1997 | Wilding | |
| 5,714,380 A | | 2/1998 | Neri et al. | |
| 5,827,480 A | * | 10/1998 | Haff et al. ................ | 422/68.1 |
| 5,849,208 A | | 12/1998 | Hayes | |
| 5,856,174 A | * | 1/1999 | Lipshutz et al. ........ | 435/286.5 |
| 5,955,351 A | | 9/1999 | Gerdes et al. | |
| 6,054,277 A | * | 4/2000 | Furcht et al. ............ | 435/6 |
| 6,071,395 A | * | 6/2000 | Lange ................ | 204/602 |
| 6,093,370 A | * | 7/2000 | Yasuda et al. ............ | 422/68.1 |
| 6,126,804 A | * | 10/2000 | Andresen ............... | 204/601 |
| 6,379,929 B1 | * | 4/2002 | Burns et al. ............ | 435/91.2 |
| 2003/0027203 A1 | * | 2/2003 | Fields ................. | 435/6 |

FOREIGN PATENT DOCUMENTS

| | | |
|---|---|---|
| DE | 2343987 | 1/1975 |
| EP | 0636413 | 2/1995 |
| WO | 9849340 | 11/1998 |

* cited by examiner

*Primary Examiner*—Suryaprabha Chunduru
(74) *Attorney, Agent, or Firm*—McDonnell Boehnen Hulbert & Berghoff LLP (57) ABSTRACT

A system for simple nucleic acid analysis is described in which the amplification space contains at least a part of the binding space. An additional improvement is achieved by the design of the binding or/and amplification space which is optionally surrounded by a heatable metal layer.

16 Claims, 7 Drawing Sheets

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
gggattcctg taacaacaag tcagg                                   25

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
cctcttcccc agaacaataa gaacac                                  26

<210> SEQ ID NO 3
<211> LENGTH: 21
<212> TYPE: DNA
<213> ORGANISM: Artificial Sequence
<220> FEATURE:
<223> OTHER INFORMATION: Detection probe

<400> SEQUENCE: 3
gtctctcatc gagacaaagt g                                       21
```

SYSTEM FOR SIMPLE NUCLEIC ACID ANALYSIS

BACKGROUND OF THE INVENTION

1. Field of the Invention

The present invention concerns a system for simple nucleic acid analysis.

2. Description of the Related Art

In the known systems for nucleic acid analysis, the nucleic acids are firstly bound in order to purify or isolate the analyte to be detected. The binding is usually carried out in vessels with relatively large volumes of several $cm^3$ in order to hold the required amount of sample, binding buffer etc. for a sensitive detection. Since detection limits of 1 to 10 analytes per ml sample have to be achieved in the diagnostic field, correspondingly large amounts of sample and thus large reaction volumes are necessary for sensitive diagnostic methods. Smaller sample volumes lead to less sensitive methods and to the risk that the analyte to be detected does not happen to be present in the selected portion of the sample which is in fact positive and would lead to a false-negative diagnostic result.

On the other hand a nucleic acid amplification of the isolated DNA analyte which is required for the detection should, however, be carried out in vessels that are as small as possible in order to achieve an adequately high amplification rate. As a consequence of this contradiction the nucleic acids immobilized for purification usually have to be eluted from the binding space and transferred into an amplification space which is different from the binding space. Devices for nucleic acid analysis using multichamber systems are described for example in EP 0 754 725; WO 95/11454; U.S. Pat. No. 5,645,801; WO 97/02357; U.S. Pat. No. 5,714,380; EP 0 733 714; EP 0 674 009; U.S. Pat. No. 5,725,831; U.S. Pat. No. 5,639,428; WO 97/10056; WO 94/05414; WO 96/41864; U.S. Pat. No. 5,589,136; WO 97/00726; EP 0 838 025; WO 97/03348; EP 0 594 260; EP 0 594 259; U.S. Pat. No. 5,288, 463; U.S. Pat. No. 5,422,271; U.S. Pat. No. 5,593,838; WO 93/22053; WO 93/22054; WO 93/22055; WO 93/22058 and WO 96/15269. However, these devices require transfer of the isolated nucleic acids from one vessel into another which, however, involves additional measures and a risk of losing a part of or the entire analyte to be detected or of contaminating the sample during the transfer.

SUMMARY OF THE INVENTION

There is therefore a need for methods of nucleic acid analysis which can overcome the disadvantages of the known methods and which in particular have a high sensitivity and can reduce the technical complexity and time required for an analysis.

This object is achieved according to the invention by a method for detecting nucleic acids in a sample comprising the steps:

(a) purifying the nucleic acids in a binding space during which the nucleic acids are immobilized and separated from impurities, (b) eluting the immobilized nucleic acids, (c) amplifying the purified nucleic acids in an amplification space and (d) detecting the amplification products in a detection space which is characterized in that the amplification space contains at least a part of the binding space.

Due to the fact that the amplification is carried out in at least a part of the binding space it is possible to considerably improve the nucleic acid analysis with regard to the technical complexity and time required. According to the invention it is possible to use the same space or a part of the space for the immobilization as well as for the amplification and the sample, which is optionally mixed with other reagents, is passed through the binding space at least once and preferably several times for the immobilization.

Systems for nucleic acid analysis invariably comprise one or several of the following steps: sample preparation, amplification, detection and evaluation.

DETAILED DESCRIPTION OF THE INVENTION

The sample preparation which can optionally be carried out before purification of the nucleic acid in step (a), can comprise a lysis of samples containing nucleic acids. Such a lysis is preferably carried out when the sample to be examined contains cells or/and cellular components. Cells can for example be lysed by adding lytic reagents, especially chaotropic reagents or lytic enzymes. In a particularly preferred embodiment a chaotropic reagent is placed in a double plunger syringe. The sample is aspirated into the syringe and the syringe opening is subsequently closed for example by a valve or a tap. The sample containing nucleic acids and the chaotropic reagent are intensively mixed by a reciprocating motion of the second plunger of the double plunger syringe. If desired the lysis can be carried out by heating the mixture at an elevated temperature preferably of 30° C. to 70° C. The lysis is achieved in particular by exerting shear forces on the sample containing nucleic acids.

The sample preparation also includes a purification step in order to separate sample components which may interfere with the subsequent detection. The nucleic acids are purified according to the invention in a binding space where the nucleic acids are immobilized and separated from impurities. The nucleic acids can for example be immobilized by covalent or adsorptive binding in the binding space. In addition it is also possible to bind the nucleic acids by means of high affinity interactions such as a sequence-specific binding using hybridization probes or binding partners of high affinity binding pairs such as avidin/biotin or specific antibodies. The nucleic acids are preferably immobilized by adsorptive binding for example to a glass surface. Binding the nucleic acids to the surface can be supported by adding suitable binding reagents such as isopropanol, chaotropic salts etc..

The binding preferably takes place on an inner surface of the binding space but it is also possible to bind the nucleic acids to arrangements introduced into the binding space such as packings or beds.

If it is intended to analyse a sample containing cells such as microorganisms, it may be advantageous to firstly capture or isolate the cells e.g. infectious organisms, by means of specific antibodies and especially antibodies that are specific for surface antigens or by means of unspecific adsorptive binding to the surface of the binding space. Thus for example appropriate antibodies can be immobilized in the binding space in order to specifically bind microorganisms such as infectious organisms. It was shown that cells such as Chlamydia can be bound adsorptively to surfaces, preferably to surfaces made of polystyrene and purified in this manner. The nucleic acids themselves can then be detected after lysis of the cells which can for example be achieved by heat treatment during the amplification reaction.

An at least partial capillary space is particularly preferably used as a binding space. In a preferred embodiment the nucleic acids or cells are immobilized on the inner surface of a capillary which is composed of glass and in particular boron silicate or polystyrene. The capillary space can, however, also be configured as a gap for example between two cover plates. The opening or the diameter of the capillary space is preferably $\geq 0.05$ mm, particularly preferably $\geq 0.5$ mm and most preferably $\geq 0.9$ mm and preferably $\leq 5$ mm, particularly preferably $\leq 2$ mm and most preferably $\leq 1.1$ mm. Whereas only a part of the binding space and in particular $\geq 10\%$, preferably $\geq 20\%$ of the entire binding volume may be in the form of a capillary space, it is preferable that almost the entire binding space, preferably $\geq 80\%$ and in particular $\geq 90\%$ of the total volume of the binding space is in the form of a capillary space.

For the immobilization a capillary is for example docked onto the double plunger syringe described above and the sample containing nucleic acids or the mixture obtained after lysis is passed at least once, preferably at least five times, more preferably at least ten times and most preferably at least twenty times through the capillary. The repeated passage of the sample or the lysis mixture through the binding space enables an advantageous increase in the yield of immobilized nucleic acids and thus an increase of the sensitivity of the overall method.

The volume ratio of binding space to sample containing nucleic acids is preferably at least 10:1 particularly preferably at least 20:1.

A large ratio of binding space to sample is advantageous since it enables a large sample volume which is necessary for a high sensitivity in the binding and at the same time allows the method to be carried out in a small space, in particular in a capillary space, as required for the subsequent amplification of the nucleic acids. A high ratio of sample volume to the volume of the binding space can be obtained if the binding space is not filled with sample which is common in the prior art but rather is passed at least once and preferably several times through the binding space.

In a further preferred embodiment the nucleic acids are bound to the surface of a glass fleece in a packing for example in a cartridge which is docked onto the capillary described above. In this embodiment the sample or lysis mixture containing nucleic acids is passed at least once through the packing during which the nucleic acids bind to the surface of the glass fleece as they flow through the packing.

Impurities that are present in the sample are separated after or at the same time as the nucleic acids immobilization which allows a selective and sensitive detection of nucleic acids. Impurities can for example be separated by treating or rinsing the binding space on which the nucleic acids are immobilized with a washing buffer. The washing buffer is preferably slowly passed at least once through the binding space and preferably contains 70 to 80 volume % ethanol.

Further purification can be achieved by drying the binding space in order to remove the washing buffer by for example heating it to about 80° C. and simultaneously passing air or an inert gas through the binding space. It is advantageous to remove residual washing buffer, especially residual alcohol, since alcohol residues could inhibit or interfere with the subsequent amplification.

At the end of step (a) the nucleic acids are preferably in a dried on form and immobilized in the binding space and preferably bound adsorptively to a glass surface.

In order to prepare for the amplification, the immobilized nucleic acids are eluted in step (b). The elution can be carried out with suitable elution solutions known to a person skilled in the art. Nucleic acids can for example be detached from a glass surface by a reagent mixture with a low salt content. A solution is particularly preferably used for elution which already contains all reagents required for the amplification. In a preferred embodiment the nucleic acid is detached from the surface in particular a glass or polystyrene surface, by drawing up a master mix into the binding space, in particular a capillary. In this case elution is in particular understood as a detachment of the immobilized nucleic acids from the surface whereby the eluted nucleic acids are not removed from the binding space. If for example the infectious organisms are purified by adsorptive binding to polystyrene in the sample preparation step, these are preferably not lysed until the start of the amplification step. Hence non-lysing buffers are required for the sample preparation step.

Afterwards in step (c) the purified nucleic acids are amplified in an amplification space. Since according to the invention the amplification space contains at least part of the binding space, it is not necessary to transfer or transport the eluted nucleic acids and thus the associated losses in yield can be avoided. The amplification is preferably carried out by means of the polymerase chain reaction (PCR). The advantage of this amplification method is that it can be used universally and has a high specificity and sensitivity. It is of course also possible to use other amplification methods known to a person skilled in the art such as isoCR, LCR, Champ, SDA, Qβ replicase, NASBA3SR, CPT, TMA, rRNA hybridization or bDNA methods. The most advantageous amplification method for each case can be easily determined by a person skilled in the art depending on the analyte and other general conditions.

It is preferable to use an amplification space that can be thermostatted. It has proven to be particularly advantageous to surround the amplification space with a heatable layer of metal since this enables rapid heating and thus short heating cycles.

In a preferred embodiment using the polymerase chain reaction, the lower end of the binding space, in particular a capillary, is firstly closed with a first stopper. Afterwards the capillary can be removed from the double plunger syringe described above and closed with a second stopper. The binding space then serves simultaneously as an amplification space.

If a capillary with a heatable layer of metal is used as an amplification space, the capillary is heated by conducting an electric current through the capillary or through the electrically conductive outer coating of the capillary. The desired temperature can be easily derived and controlled on the basis of the temperature coefficient and the electrical resistance. Cooling of the amplification space can for example be accelerated by for example blowing in ambient air although if a capillary is used as the amplification space a rapid cooling rate is obtained anyway after switching off the heating current as a result of the low mass. The preferred use according to the invention of a capillary surrounded with a heatable layer of metal allows a thermocycle of 92° C., 55° C., 72° C. in less than 25 sec due to the high heating and cooling rates.

The products formed in the amplification are detected according to the invention in order to detect the nucleic acids present in the sample. The detection can be carried out by known methods. The detection is preferably carried out online by fluorescence.

In a particularly preferred embodiment the detection space contains at least part of the amplification space or/and at least a part of the binding space. It is particularly advantageous with regard to the simplicity of the method when all steps of the detection method i.e. the purification of the nucleic acids, the amplification of the purified nucleic acids and the detection of the amplification products are carried out in the same reaction space, in particular in a capillary.

Thus in the preferred embodiment described above of a capillary that can be closed with a stopper which is used as a binding and amplification space, a beam of excitation light can be passed through an optical window in the stopper and the light emerging through a window on the same stopper or on a stopper on the opposite side can be measured to carry out a fluorescence detection. The change of absorbance can also be used for the detection in the same manner.

The intensities of the excitation light and of the fluorescent light can then be offset against one another to obtain a signal. The plot of signal intensity versus the number of amplification cycles can be used for a qualitative detection and also for a quantitative determination of the concentration of an analyte. This enables a preliminary diagnostic decision by for example comparing the number of cycles at which a significant increase in the signal begins with a previously defined threshold.

The test can be further improved by adding a defined amount of an internal standard and the accompanying probes and labels in which case the amplification can be monitored for a possible inhibition by test reagents or/and impurities present in the sample. It is preferable in this case to detect the internal control and the analyte at two different wavelengths which allows the analysis and control to be carried out simultaneously.

The method can be additionally controlled by comparing the temperature kinetics during the heating of the amplification space with previously determined standard values from which it is possible to deduce the degree of filling of the amplification space and especially of a capillary. If the amplification space loses liquid during the amplification this leads to changes in the heating kinetics and to an error message when a previously defined tolerance limit is exceeded.

In order to further simplify the method all steps are preferably carried out in a closed device i.e. in an integrated device which contains all necessary reaction spaces and reagents.

The method according to the invention is especially suitable for point of care (PoC) tests since in addition to a comparable performance with standard laboratory methods, it allows a simple handling without elaborate apparatus, low production costs and an uncomplicated analysis. The integration of the sample preparation with the subsequent amplification eliminates pipetting steps and associated contamination problems.

The method according to the invention is particularly suitable for detecting pathogens in biological samples. It enables a simple and rapid detection of germs, for example Chlamydia or others.

The invention also concerns a device for detecting nucleic acids in a sample, in particular by a method as described above, comprising:
(a) a binding space to purify nucleic acids, in which the nucleic acids are immobilized and separated from impurities,
(b) an amplification space to amplify nucleic acids,
(c) a detection space to detect nucleic acids and optionally
(d) reservoirs or/and supply lines for the sample or/and reagents, which is characterized in that the amplification space contains at least a part of the binding space.

The device according to the invention is an integrated system. The detection space preferably also contains at least a part of the amplification space or/and of the binding space. The binding and/or amplification space can be at least partially in the form of a capillary space which results in the advantages described above.

A prerequisite for detecting nucleic acids in a sample is that nucleic acids that are enclosed or bound in aggregates have to be firstly released in order to make them accessible for analysis. For this purpose cells are for example treated with lytic enzymes in order to disrupt the cell wall and release the nucleic acids contained in these cells. However, such a lysis is very time consuming.

WO 95/18851 describes a method for reducing the size of high molecular structures in which the sample is passed through porous layers in order to facilitate the size reduction by shearing. However, a problem with this is that the desired analyte is also at least partially retained in the pores and thus the sensitivity of the entire detection method is impaired.

Another object was therefore to provide a method for lysing aggregates containing nucleic acids which enables the nucleic acids to be released in a short time and without loss of yield.

This object is achieved according to the invention by a method for lysing a matrix containing nucleic acids or aggregates containing nucleic acids which is characterized in that a lysis mixture which comprises the matrix containing the nucleic acids and a lysing reagent is moved through a capillary space which breaks up the matrix and releases the nucleic acids contained therein.

High shear forces are required to lyse matrices containing nucleic acids in order to lyse the samples in a short time. In a method according to the invention high shear forces are obtained by using a capillary space and moving the sample, for example by passing or transporting the sample through the capillary space which facilitates the lysis of the matrix containing nucleic acids.

Lysis is understood as any disruption or reduction in size of a matrix containing nucleic acids in which the nucleic acids that are enclosed in the matrix or bound to the matrix are released. The disruption is preferably a lysis. The matrix containing nucleic acid is preferably cells or/and cell fractions. However, other structures can be lysed that contain enclosed nucleic acids or nucleic acids in a bound form such as micelles etc.

The lysing reagent is used according to the invention to facilitate the release of nucleic acids. A lysing reagent is preferably used which contains a lytic enzyme and/or a chaotropic substance. The lysing reagent should fundamentally be able to dissolve or attack aggregates containing nucleic acids.

A glass capillary or/and a polystyrene capillary and in particular a capillary coated with boron silicate is preferably used as the capillary space. This has the advantage that, in addition to generating the high shear forces which facilitates the lysis, the same space can also be used for immobilization and further treatment or processing of the released nucleic acids as described above. The capillary space can be also a plunger with capillary holes or a gap between a vessel wall and a plunger. The sample is preferably passed several times through the capillary space, in particular more than five times and particularly preferably more than ten times in order to achieve a rapid lysis. The volume ratio of the lysing mixture to the capillary space is in this case preferably more than 10:1, particularly preferably more than 20:1. If the sample is passed through the capillary space, it is possible to use a large sample volume which results in a high sensitivity and keeps the capillary space small which has advantages with regard to the overall configuration and in particular with regard to a subsequent amplification.

A further aspect of the invention concerns a method for isolating nucleic acids from microorganisms which is characterized in that a sample containing microorganisms is contacted with a polystyrene surface under conditions in which the microorganisms bind to the polystyrene surfaces and other sample components are separated and the nucleic acids are isolated from the microorganisms. It was surprisingly found that polystyrene surfaces are excellently suitable for sample preparation for nucleic acid analysis. Vessels which have a polystyrene surface can be used for sample preparation in nucleic acid analysis which allows provision of a highly integrated device. Polystyrene has numerous advantages over the glass surfaces that were previously used for immobilization such as easy machinability, low weight and mechanical stability even with small wall thicknesses.

The inner wall of a binding space coated with polystyrene or made of polystyrene is for example suitable as a polystyrene surface and it is also possible to use small polystyrene balls or polystyrene beads etc. A polystyrene capillary is preferably used. In order to increase the yield and in order to keep the binding space as small as possible, the sample can be passed several times over the polystyrene surface.

As described above a major goal in the development of nucleic acid test methods is to reduce the amount of apparatus and/or of time required. The heating and cooling cycles necessary to carry out an amplification require a considerable amount of time which is why it would be advantageous to provide a method in which this time is reduced.

A further aspect of the invention therefore concerns a method for the amplification of nucleic acids comprising steps at different temperatures which is characterized in that the amplification is carried out in a space which is surrounded by a heatable metal layer. The use of a heatable metal layer which preferably surrounds the whole surface of the amplification space enables short heating rates to be achieved. Cooling can then be accelerated in a conventional manner for example by blowing air onto it or by using other cooling technologies. However, the amplification is preferably carried out in a capillary space. Due to the low mass of such a capillary space, the heating and cooling rate can be further increased. A glass or/and polystyrene capillary is preferably used which is surrounded by a heatable metal layer and preferably by a metal layer that covers the complete surface.

The invention also concerns a capillary reaction vessel to carry out an amplification of nucleic acids which is surrounded by a heatable metal layer.

Aspects of the invention mentioned above can either be used alone or in any combination in order to improve nucleic acid analysis. The said improvements are also of particular advantage with regard to being able to automate the entire process. A simple and rapid nucleic acid analysis can be used in particular for control analyses which are intended to give information about whether more extensive and complicated test procedures should be carried out at all. The methods are also suitable for the simultaneous examination of several samples.

The invention is further elucidated by the attached figures and the following examples in which FIGS. 1 to 7 show a preferred procedure of the method according to the invention.

Figure 1:
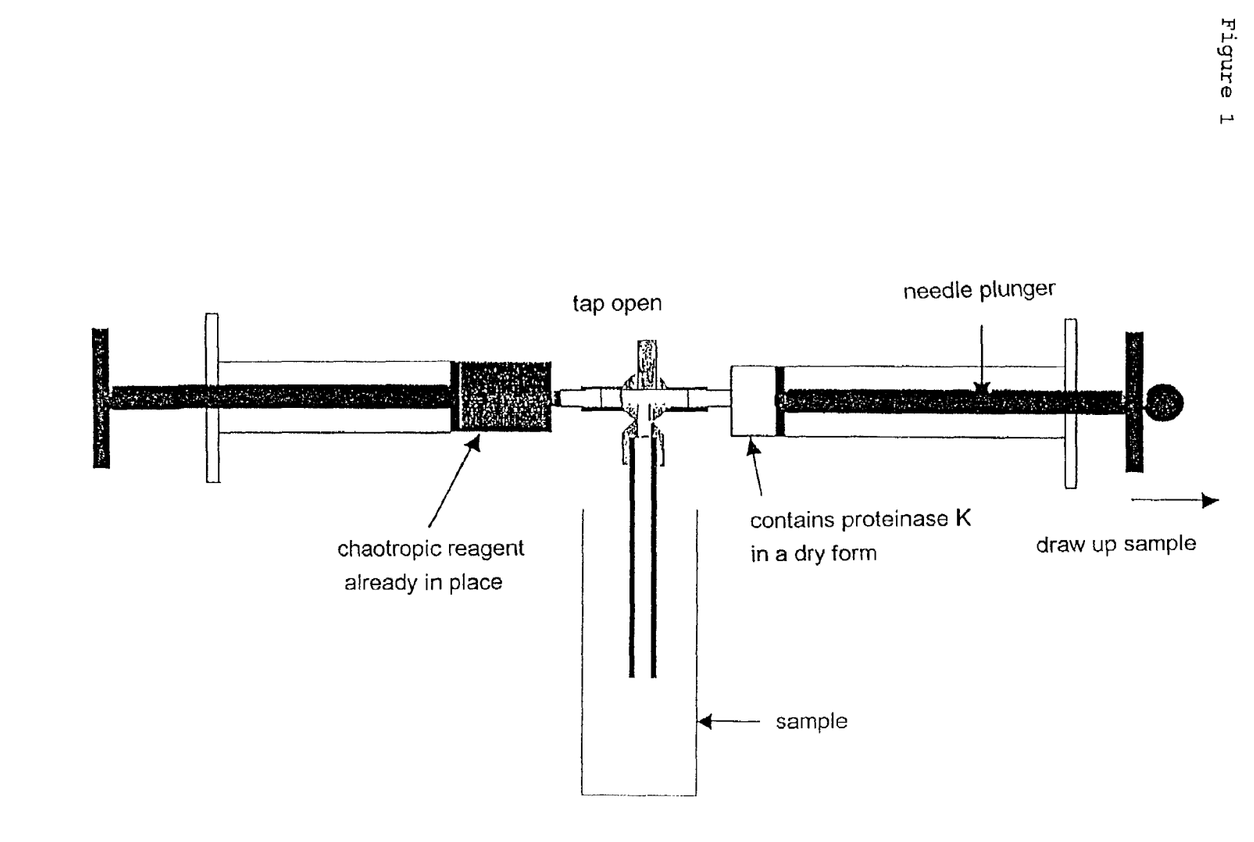
FIG. 1 is a diagram depicting a syringe arrangement in accordance with a preferred embodiment of the invention.

FIG. 1 shows a syringe arrangement for drawing up a sample containing cells in which a chaotropic agent is placed in the left syringe and dry proteinase K is placed in the right double chamber syringe with a needle plunger. The sample is sucked in from a storage vessel by operating the plunger of the right syringe.

Figure 2:
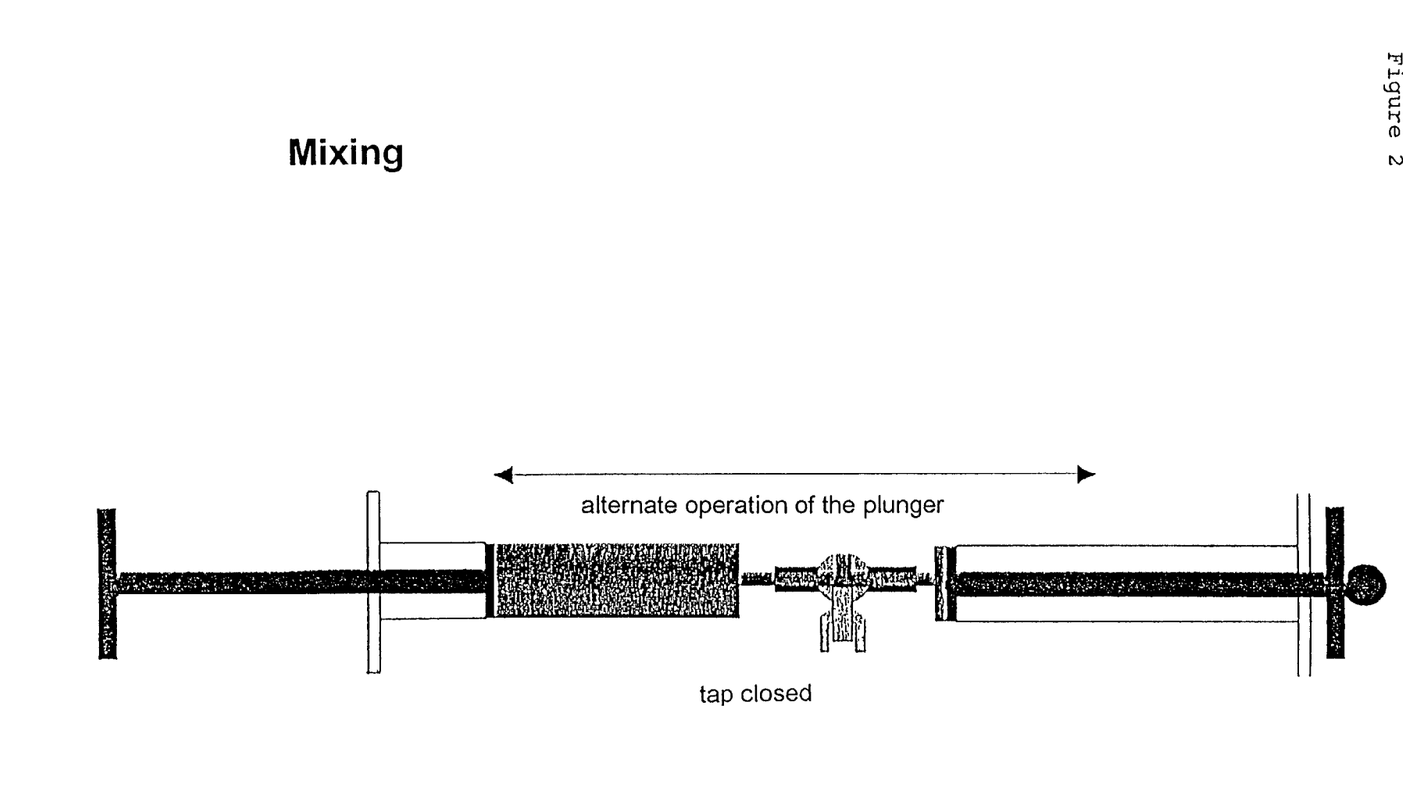
FIG. 2 is a diagram depicting the mixing of a sample with reagents in accordance with a preferred embodiment of the invention.

FIG. 2 shows the mixing of the sample with the reagents that were already in place and the lysis of aggregates containing nucleic acid. For this the plungers of the syringes were operated alternately and the lysis was facilitated by sliding the mixture through a capillary space between the syringes.

Figure 3:
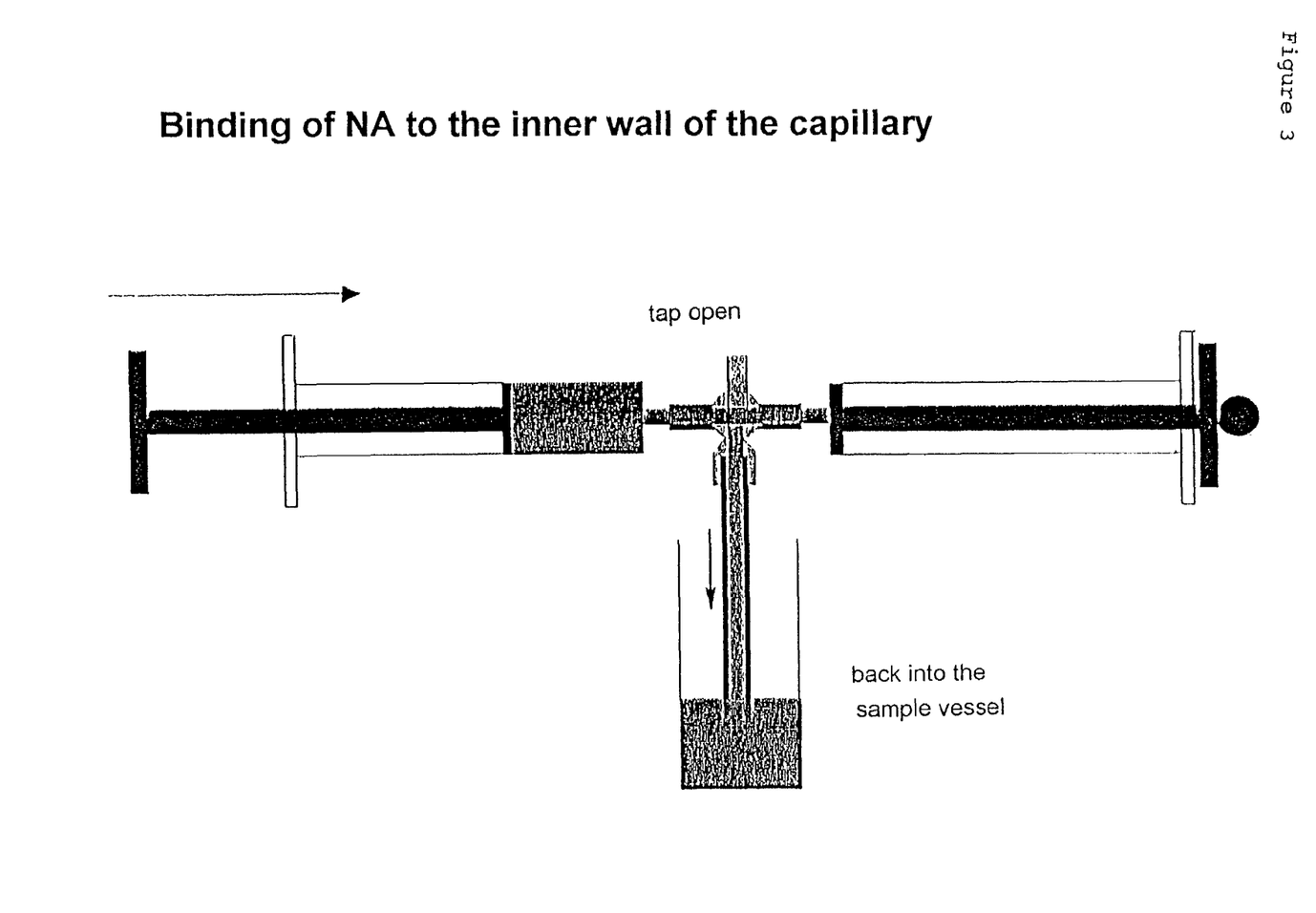
FIG. 3 is a diagram depicting the binding of released nucleic acid to an inner wall of a capillary in accordance with a preferred embodiment of the invention.

FIG. 3 shows the binding of the released nucleic acid to an inner wall of the capillary. For this the sample is pressed once and preferably several times back into the sample vessel through a capillary and is optionally sucked in again.

Figure 4:
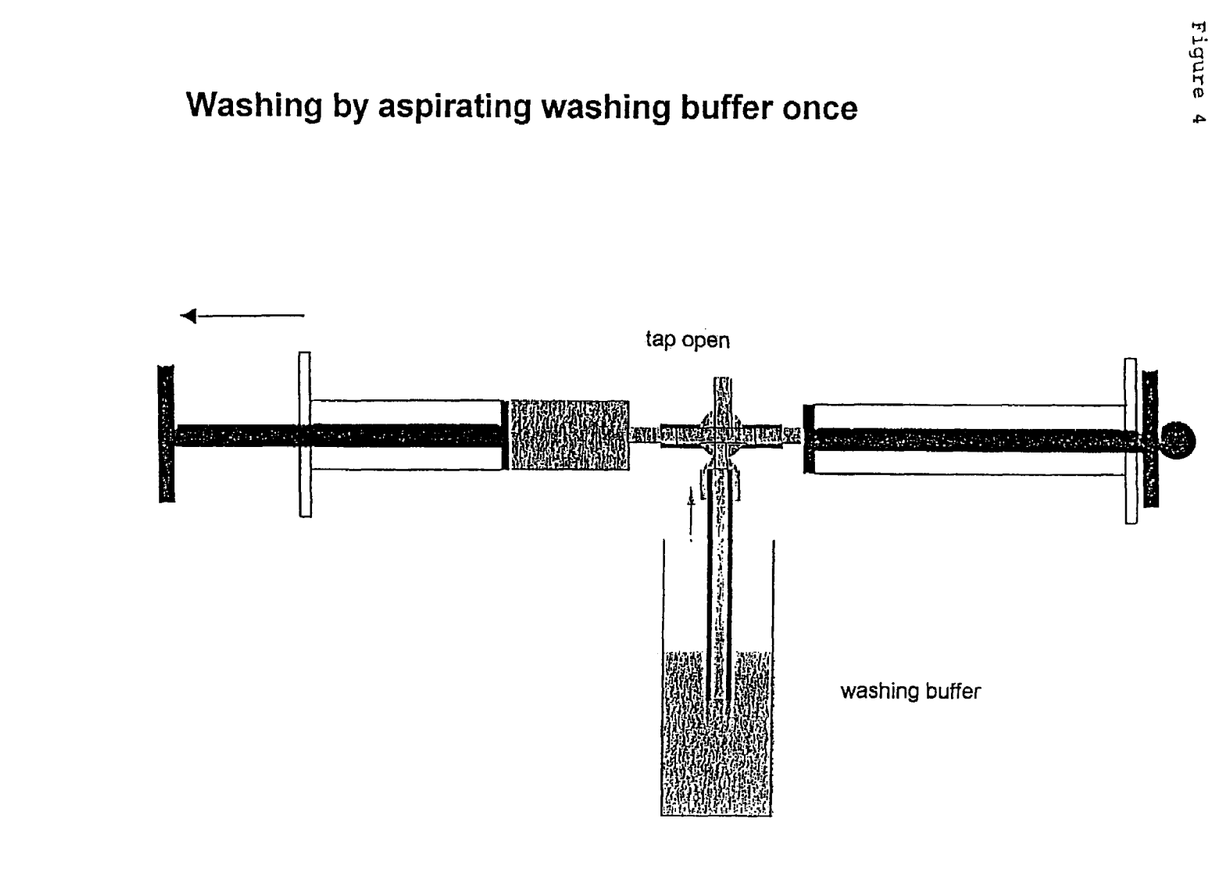
FIG. 4 is a diagram depicting a washing step in accordance with a preferred embodiment of the invention.

FIG. 4 shows the washing of the immobilized nucleic acids on the inner side of the capillary by sucking up the washing buffer once.

Figure 5:
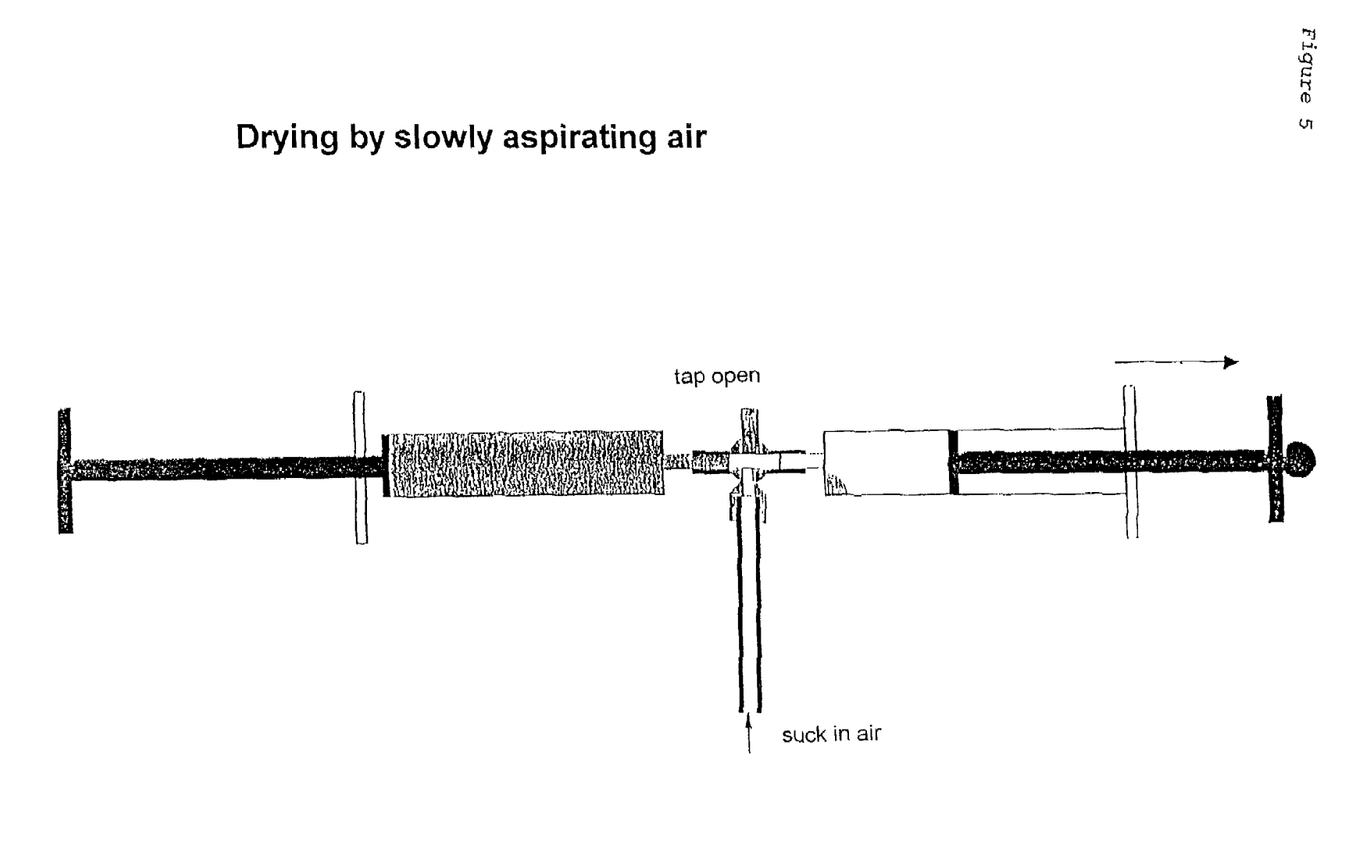
FIG. 5 is a diagram depicting a drying step in accordance with a preferred embodiment of the invention.

FIG. 5 shows the drying of the washed immobilized nucleic acids by slowly sucking in air.

Figure 6:
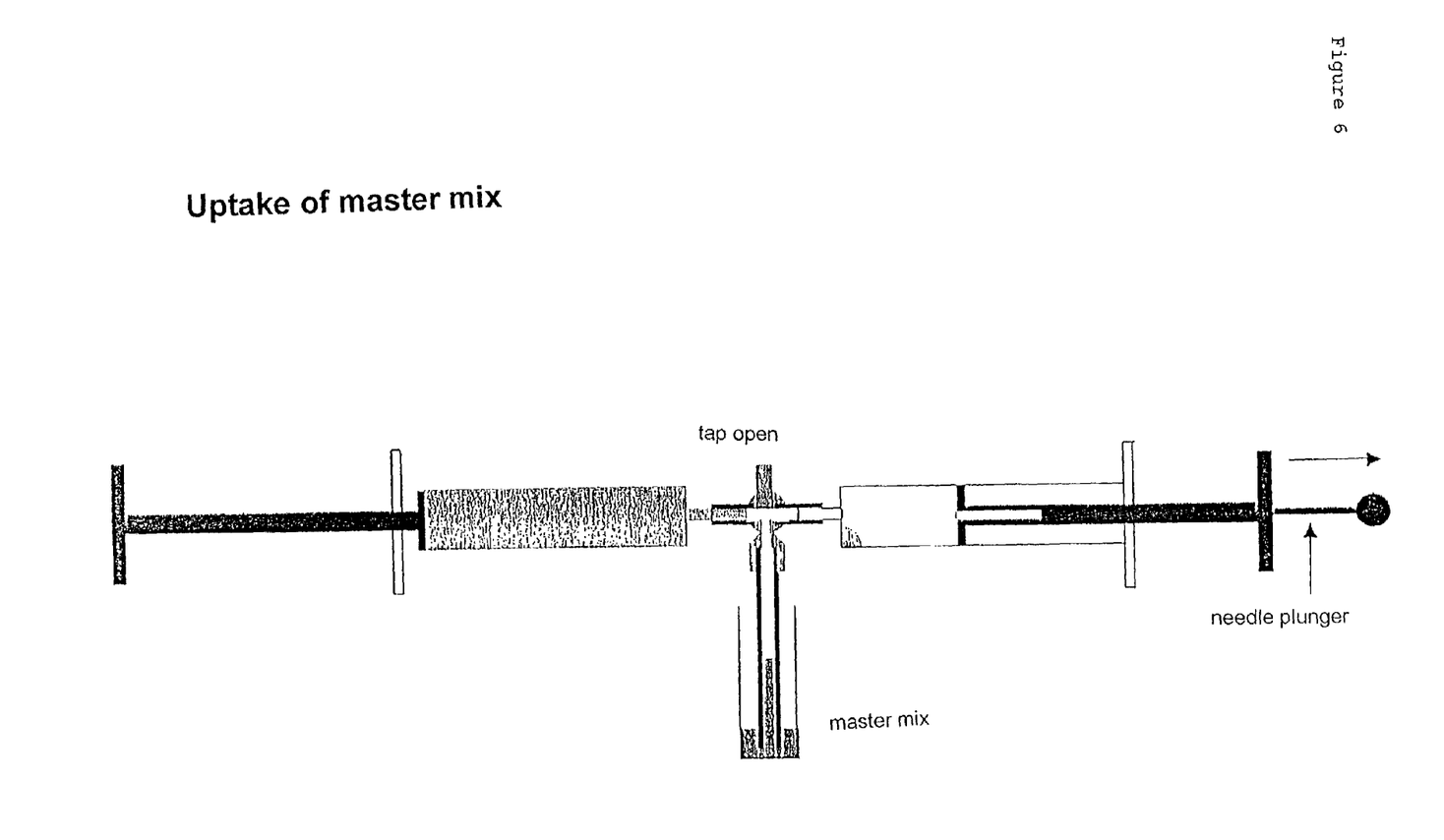
FIG. 6 is a diagram depicting the uptake of a master mix in accordance with a preferred embodiment of the invention.

FIG. 6 shows the uptake of the master mix into the capillary during which the master mix elutes the immobilized nucleic acids and at the same time contains all necessary reagents for the subsequent amplification.

Figure 7:
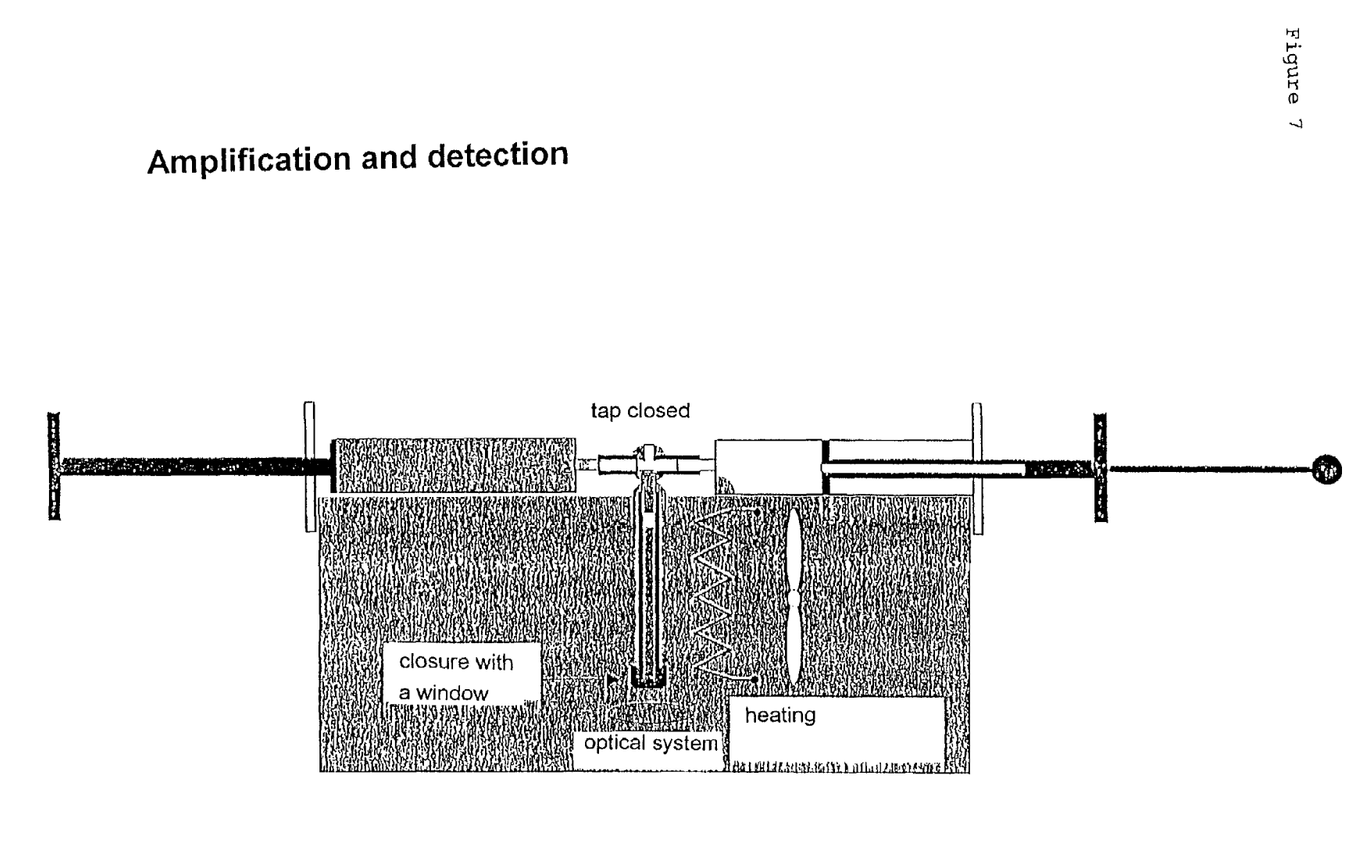
FIG. 7 is a diagram depicting the amplification, and detection of the amplification products, in accordance with a preferred embodiment of the invention.

FIG. 7 shows the amplification and detection of the amplification products. For this the capillary is closed with a stopper which contains a window. After the amplification has been carried out, the detection takes place by shining light through the optical system that is shown (for example by means of fluorescence detection).

EXAMPLES

1. Double Plunger Syringe for Performing the Method According to the Invention

The double plunger syringe essentially corresponds to a conventional disposable syringe made of polypropylene. It has a valve or stop tap between the body of the syringe and the outlet. The double plunger is designed such that the push rod for the mixing plunger runs inside the main plunger.

The main plunger has two sealing areas at its lower end. On the one hand a seal against the syringe and, on the other hand a seal against the push rod of the mixing plunger. The main plunger is moved by a push cylinder which projects beyond the body of the syringe and the upper end of which is designed such that it can be securely held and moved by hand or alternatively by an instrument component.

The lower end of the mixing plunger forms a small gap with the wall of the syringe. The push rod of the mixing plunger runs through the bottom of the main plunger and still protrudes from the push cylinder of the main plunger in any position of the main plunger. It's upper end is designed such that it can be securely held and moved by hand or alternatively by an instrument component.

The stop tap can be operated either manually or automatically and it can permanently adopt both positions (open/closed).

The opening of the syringe for fluids is in the shape of a common cone. The cone is advantageously suitable for receiving disposable pipette tips and the amplification capillary.

2. Carrying Out the Method According to the Invention with Two Separate Syringes Instead of the double plunger syringe described above, it is also possible to join separate syringes, for example two disposable syringes made of polypropylene, via a plastic three-way tap. A disposable pipette tip is docked onto the three-way tap by means of a cone in order to aspirate reagent or sample. The liquid is then taken up into one of the syringes by pulling the syringe plunger. Further liquid can be also sucked into the same syringe. For the mixing the three-way tap is set such that the two syringes are linked and the sample or reagents that have been taken up are prevented from escaping. Alternate operation of the two syringe plungers presses the liquid through the hole in the forcet key from one syringe to the other and thus mixes it under high shear forces.

3. Volume Control of the Amplification Mixture

In order to draw up an exact amplification volume into the amplification capillary, one of the plungers of the syringes is configured as a double plunger in such a manner that it holds a very small plunger centrally e.g. a plunger made of metal or plastic wire which has a diameter corresponding to the inner diameter of the amplification capillary. This allows an exact uptake of liquid into the amplification capillary and prevents an accidental aspiration of master mix and eluate into the waste container.

4. Amplification Capillary

The amplification capillary preferably has an inner diameter of ca. 1 mm and has a glass surface on the inside surface. The glass surface can be smooth or roughened or structured in order to enlarge the surface. The capillary itself can be manufactured from metal, glass or plastic and the wall is made to be as thin as possible. The outer surface is made of an electrically conducting material, preferably of metal. The electrically conducting material has an electrical resistance with a positive or negative temperature coefficient. There is a layer having a high electrical conductivity and low contact resistance at both ends of the capillary in order to form an electrical contact between the capillary and the instrument. When an electrical voltage is applied, current flows which heats the conductive layer and thus the capillary. The current depends on the temperature and can thus also be used to measure the temperature.

The amplification capillary is preferably provided with closure stoppers which are made of plastic and in particular of an optically clear material. Polycarbonate and polypropylene are particularly preferred. The closure stopper is preferably designed such that a stopper projects into the interior space of the capillary and its outside is surrounded by an outer casing. Light can be radiated out of or into the side facing the capillary. For this purpose an optical element such as a window or a lens can be integrated into the closure stopper. An electrically conductive element e.g. a wire can additionally be integrated into the wall of the outer casing of the stopper which makes an electrical contact when the stopper is pressed onto the capillary.

5. Syringe Containing a Glass Fleece as the Binding Phase (Syringe Front Filter)

In order to bind nucleic acids after chaotropic lysis to a glass fleece surface, a glass fleece was integrated into a syringe front filter. It is not advantageous to directly insert the glass fleece in the amplification space due to a possible inhibition of the glass fleece material during the amplification reaction e.g. a PCR reaction. 250 µl cell culture supernatant containing Chlamydia (1%) was lysed by chaotropic lysis. The lysate was passed over the glass fleece by means of a disposable syringe in order to bind the nucleic acids. Corresponding solutions of the High Pure Plasmid Isolation Kit (Boehringer Mannheim Cat. No. 1754777) were used as the lysis, washing and elution buffer. The composition of the glass fleece used in the experiments was identical to the glass fleece of the filter tubes of the High Pure Isolation Kit. It was subsequently washed with washing buffer and dried with air. Care must be taken that alcohol residues are removed as completely as possible from the washing buffer. Subsequently the nucleic acids were eluted and the PCR amplification and gel detection were carried out. The nucleic acid was preferably eluted with the master solution which already contains all reagents required for the amplification. Although it was found that passage through the fleece led to an amplification loss during the PCR reaction ($10^5$ CT plasmids), this is, however, compensated by the high binding capacity and high binding rate of the glass fleece material.

PCR Protocol

The oligonucleotides CP24 5'GGGATTCCTGTAACAA-CAAGTCAGG-3' (SEQ ID NO:1) (position 195-219 of pCTT1) and CP27: 5'-CCTCTTCCCCAGAACAATAA-GAACAC-3' (SEQ ID NO:2)(position 40 1-376 of pCTT1) optionally in a 5' biotinylated or 5' digoxigenylated form were used as primers for the amplification.

The reaction volume was 100 µl (4 mM $MgCl_2$, 0.1 mM of each dNTP, 300 mM primer CP24 and CP27, 2.5 U Taq polymerase, 2 U UNG (uracil DNA glycosylase) and template in PCR buffer (Roche Diagnostics Catalogue No. 1600753).

The reaction procedure was as follows:

10 min 37° C., 5 min at 95° C., 1 min at 60° C.

34 cycles each of 30 s at 95° C. and 60 s at 60° C.

10 min at 72° C.

keep at 50° C.

6. Syringe with a Glass Capillary as the Binding Phase

An important advantage of preparing samples in a glass capillary, for example in combination with a syringe, is the simple manual operation and the simple integration with the subsequent amplification. The capillary used for the sample preparation with the nucleic acids bound thereto can be used directly for the amplification after filling with master mix. The sample preparation space is thus also the amplification space. The use of a glass capillary enables a rapid amplification as well as an online detection and thus represents a highly integrated overall solution for nucleic acid tests.

The sample material is preferably passed several times through the glass capillary for example by means of a peristaltic pump with incubation times of about 20 min. It is, however, also possible to pass the solution containing sample through the capillary using a manually operated syringe with an incubation period of only 1 min which still results in an adequate sensitivity of the test. In this case it is also particularly advantageous to directly use a master mix solution to elute the immobilized nucleic acids so that the amplification step, for example a PCR, can be carried out with omission of a separate elution step.

7. Syringe with a Polystyrene Capillary as a Binding Phase

It was found that microorganisms can be bound to polystyrene surfaces in an aqueous medium. Thus for example Chlamydia bind to a polystyrene disposable inoculating loop in a 20 minute incubation step and can be transferred directly into a PCR reaction mixture. Hence polystyrene capillaries were used in conjunction with a disposable syringe in order to produce a highly integrated device for a Chlamydia nucleic acid test. With an incubation period of 1 min for a sample containing Chlamydia, it was possible to achieve a sensitivity between 0.1 and 0.01% cell culture supernatant depending on the dilution medium ($H_2O$, PBS or urine).

In order to prepare polystyrene capillaries, standard polystyrene reaction vessels (Sarstedt) were pulled out to form capillaries after heating and used in combination with a disposable syringe. It turned out that the polystyrene capillaries were very suitable for preparing samples of nucleic acids. With such a sample preparation it was possible to still detect 300µl of a 0.01% cell culture supernatant as clearly positive in a subsequent PCR reaction and detection. Hence a comparable sensitivity to conventional laboratory methods was achieved using a polystyrene capillary.

8. Sample preparation with a glass capillary

A 5 µl Modulohm capillary (boron silicate glass) of 3 cm in length was used as the glass capillary. 250 µl sample +50 µl proteinase K (20 mg/ml) and 250 µl lysis reagent (5.4 M GuSCN, 20% Triton X-1100, 1% DTT, 10 mM Tris HCl, pH 6) were incubated for 10 mm at 70° C. after briefly vortexing and subsequently allowed to cool for 5 mm to room temperature. A syringe (10 ml, Becton Dickinson) was connected by a short plastic tube to the glass capillary. The lysate was aspirated into and discharged from the syringe by a steady movement over 2 mm. During this time the nucleic acids bound to the capillary. Then 800 µl washing buffer (20 mM NaCl, 10 mM Tris HCl, pH 7.5, 70 vol % ethanol) was rinsed through the capillary for 2 mm using the syringe and the capillary was subsequently dried by aspirating air for 1 mm. Then 100 µl elution buffer (10 mM Tris HCl pH 8.5) was aspirated into the capillary using the second syringe (1 ml; Becton Dickinson Co.). The PCR reaction was carried out under the conditions stated in 5. The detection was by means of a detection probe (5'-GTCTCTCATCGAGACAAAGTG-3' (SEQ ID NO:3) from the Chlamydia trachomatis plasmid pCTT [C. thrachomatis bases 1-7496] corresponding to position 354-374 of pCTT1 (Sriprakash and Macavoy, Plasmid 8(1987), 205-214) using a standard procedure.

9. Sample Preparation with a Polystyrene Capillary

Polystyrene vessels (Sarsted) were heated with a heating lamp and pulled out to form capillaries with a diameter between 1 and 2 mm. After cooling pieces of 3 cm in length were separated. A syringe (10 ml, Becton Dickinson) was connected to the polystyrene capillary via a short plastic tube. Then the sample was rinsed through the capillary by means of the syringe. Subsequently 800 µl washing buffer was sucked through the capillary by means of the syringe and the capillary was dried by aspirating air for 1 min. The amplification by means of a PCR reaction and detection by means of hybridization with a detection probe were carried out immediately afterwards as described under 8 using the polystyrene capillary or by cutting the capillary and transferring it into a PCR reaction vessel.

What is claimed is:

1. An apparatus for detecting nucleic acids in a sample, comprising:
   (a) a binding space for purifying the nucleic acids by immobilizing the nucleic acids and separating impurities,
   (b) an amplification space for amplifying the nucleic acids wherein at least a part of the amplification space is identical to a part of the binding space, and
   (c) a detection space for detecting the nucleic acids.

2. The apparatus of claim 1 further comprising reagents for purifying, amplifying and detecting the nucleic acid.

3. The apparatus of claim 1, wherein the detection space comprises a part of at least one of the amplification space and the binding space.

4. The apparatus of claim 1, wherein at least one of the binding space and the amplification space comprises a capillary space.

5. The apparatus of claim 4 wherein the capillary space is a capillary reaction vessel surrounded by a heatable metal layer.

6. The apparatus of claim 4 wherein the capillary space is glass or polystyrene.

7. An apparatus for amplifying nucleic acids comprising a capillary reaction vessel surrounded by a single heatable metal layer wherein the layer is coated on the capillary reaction vessel.

8. The apparatus of claim 1 further comprising a sample transport mechanism which transports the sample and reagents through the binding space, the amplification space and the detection space.

9. The apparatus of claim 1 wherein the binding space provides a surface for binding the nucleic acids.

10. The apparatus of claim 9 wherein the binding space is defined by an inner surface of a reaction vessel, wherein the inner surface binds nucleic acids.

11. An apparatus for detecting nucleic acids in a liquid sample, comprising:
    (a) a space comprising a capillary reaction vessel surrounded by a heatable metal layer, wherein the interior surface of the vessel binds nucleic acids;
    (b) reagents for amplifying and detecting the nucleic acids that become bound to the surface;
    (c) a sample transport mechanism which transports the sample and reagents through the space.

12. The apparatus of claim 11 further comprising reagents for purifying the nucleic acids.

13. The apparatus of claim 11 wherein the capillary space is glass or polystyrene.

14. The apparatus of claim 1 wherein the binding space is identical to the amplification space.

15. The apparatus of claim 14 wherein the detection space is identical to the binding space.

16. The apparatus of claim 5 wherein the metal layer is coated on the exterior of the vessel.

* * * * *